April 29, 1975 P. ECKE, JR Plant Pat. 3,711
POINSETTIA PLANT
Filed April 22, 1974
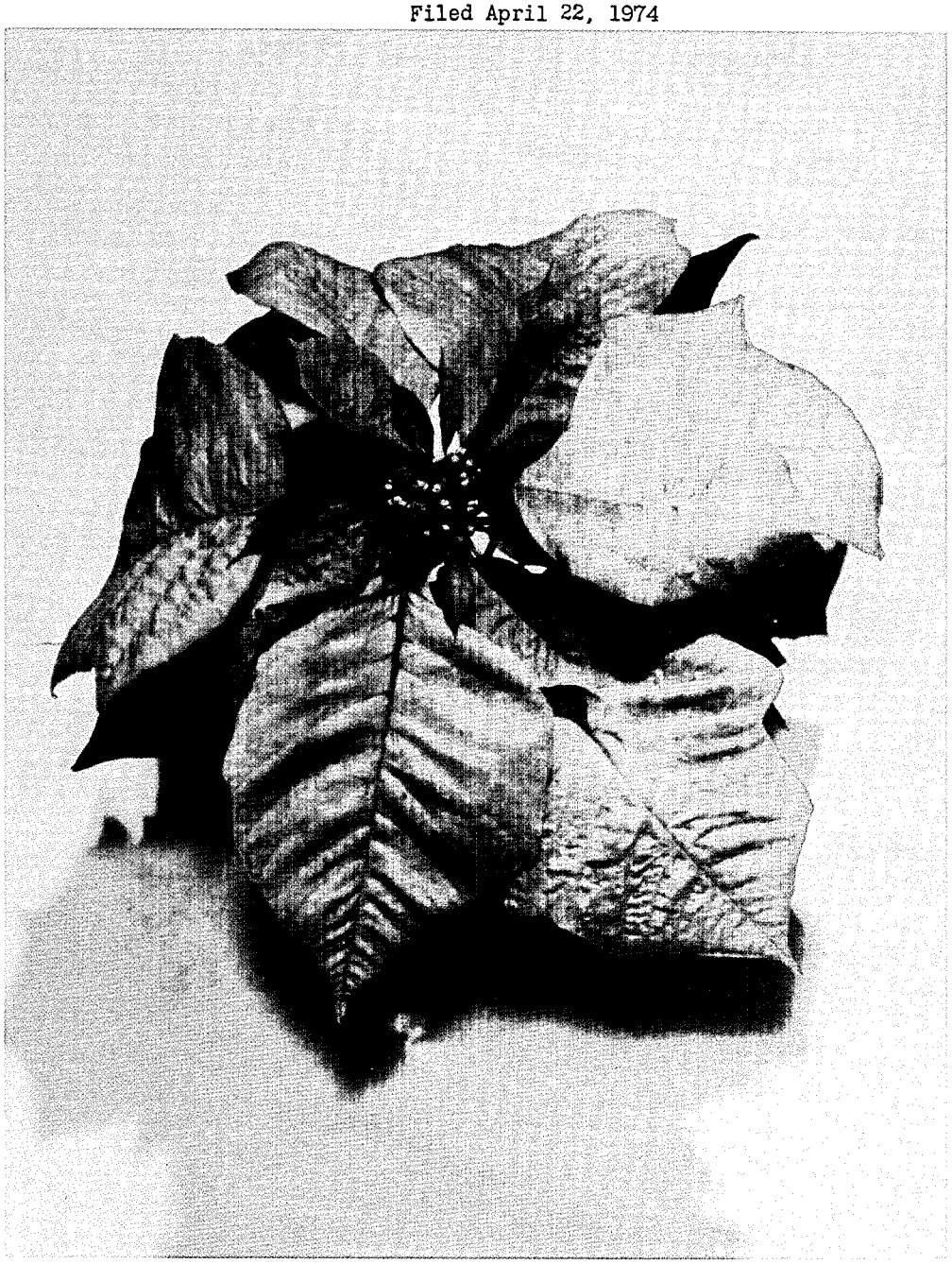

United States Patent

Plant Pat. 3,711

Patented Apr. 29, 1975

1

3,711

POINSETTIA PLANT

Paul Ecke, Jr., Encinitas, Calif., assignor to Paul Ecke Ranch, Encinitas, Calif.

Filed Apr. 22, 1974, Ser. No. 462,994

Int. Cl. A01h *5/00*

U.S. Cl. Plt.—86 1 Claim

The present invention relates to a new and distinct variety of poinsettia plant (botanically known as *Euphorbia pulcherrima*), which was originated by me by crossing two unnamed and unpatented red poinsettia seedlings.

The primary objectives of this breeding were to produce a new and improved poinsettia variety which has stiff stems that do not require staking, wider bracts than other varieties heretofore known in commerce, a compact inflorescence form which creates an attractive effect in each bloom, and which retains its foliage and bracts for an unusually long period of time after reaching maturity. These objectives were fully achieved, along with other desirable improvements, as evidenced by the following unique combination of characteristics which are outstanding in the new variety and which distinguish it from its parents, as well as from all other varieties of which I am aware:

(1) A very vigorous, tough, durable and short plant habit, with the ability to grow well as a multiple stem and multiple bloom plant;
(2) A very vigorous and extensive root system;
(3) Stiff stems which do not require staking;
(4) Retention of the bracts, foliage and inflorescences for a long period of time after reaching maturity;
(5) A habit of not requiring light to delay bud sets;
(6) A well-pinching habit which produces 3 or more breaks;
(7) A normal blooming habit at about 4° to 5° lower night temperatures than required for variety "C–1 Red" (Plant Pat. No. 2,923) during the months of October, November and December, but having the ability to be satisfactorily brought into bloom and full maturity in every month of the year through the exercise of proper greenhouse culture technique;
(8) A distinctive and attractive appearance of the bracts and their absence of any tendency to droop with age;
(9) A distinctive and attractive bright Scarlet Red general color tonality of the bracts;
(10) Absence of drooping and retention of the position of the inflorescences relative to the bracts without rising as occurs in other varieties as their inflorescences approach maturity; and
(11) Excellent keeping qualities and consequent suitability for home decoration.

Asexual reproduction of my new variety by vegetative cuttings propagated under mist at Encinitas, Calif., shows that the foregoing characteristics and distinctions come true to form and are established and transmitted through successive propagations.

The accompanying drawing shows a typical specimen plant of my new poinsettia variety as depicted in color as nearly true as it is reasonably possible to make the same in a color illustration of this character.

The following is a detailed description of my new variety, with color terminology in accordance with Wilson's Horticultural Colour Chart, except where general color terms of ordinary significance are obvious, as based on specimens grown at Encinitas, Calif.:

Parentage: Seedling.
*Seed parent.*—An unnamed red poinsettia seedling.
*Pollen parent.*—An unnamed red poinsetta seedling.

2

Propagation: Holds its distinguishing characteristics through succeeding propagations by vegetative cuttings.
Form: Short; upright; graceful contour.
Habit of growth: Vigorous grower; short.
Rooting habit: Very fast (from 12 to 15 days under mist); vigorous; extensive; uniform.
Blooming habit: Approximately 8 weeks after start of short days.
Blooming season: Naturally from October through December, but has excellent suitability for forcing in every month of the year by appropriate greenhouse culture practices; blooms well at about 4° to 5° lower night temperatures than required for the variety "C–1 Red."
Foliage: Alternate; borne horizontally on stems; persistent; normal abundance.
*Size.*—Medium; borne on short petioles; from about 3 inches to 6 inches long; from about 2½ inches to 5 inches wide.
*Shape.*—Ovate-acuminate, with usually two serrations on each edge; generally similar to "C–1 Red" (Plant Pat. No. 2,923).
*Color.*—Dark green; generally similar to "C–1 Red."
Disease resistance: Resistant to rhizoctonia and pythium stem and root rot during propagation and growing period, and very resistant to botrytis during blooming period, as determined by comparison with other varieties grown under the same conditions at Encinitas, Calif. which are infected with these diseases.
Bracts: From 20 to 25 bracts overlapping in a cascading effect; relatively long lasting.
*Size.*—From about 3 inches to 6 inches long and from about 2½ inches to 5 inches wide.
*Shape.*—Elliptic-acuminate, with some serration.
*Color.*—Bright red from near Scarlet, Plate 19/1 to near Geranium Lake, Plate 2/1.
Flowers:
*Borne.*—Continuously for several months; many flowers per stem in regular clusters in various stages of development; borne on strong, very short stems; slow development, giving a compact appearance for a greater period of time; position of the flowers remains relatively low without rising as they do in other commercial poinsettia varieties during early development, and flowers do not spread out during later stages of development, thereby presenting a more attractive appearance for a longer period of time.
*Quantity of bloom.*—Relatively abundant; flowers gradually drop off after maturity; flower clusters remain tight but new ones do not continue to develop; centers do not spread.
*Buds.*—From medium to large size; borne on light green stems.
Reproductive organs:
*Stamens.*—Few; from ⅛ inch to ¼ inch long. Color—Near Claret Rose, Plate 021.
*Pollen.*—Color—Near Naples, Yellow, Plate 403.
*Styles.*—Color—Near Rose Opal, Plate 022.
*Ovaries.*—Color—Near Lettuce Green, Plate 861.
*Nectar cups.*—Color—Near Egyptian Buff, Plate 407.
General observations: This new variety is generally similar to the vairety "C–1 Red" (Plant Pat. No. 2,923) in respect to rooting time, branching ability, leaf retention and other feautres, but is particularly distinguished therefrom by its shorter habit of growth, with production of blooms in about 8 weeks at night temperatures about 4° to 5° lower than required for "C–1 Red," and particularly distinguished by its distinctive and attractive bright Scarlet Red bract color.

I claim:
1. A new and distinct variety of poinsettia plant, sub-stantially as herein shown and described, characterized particularly as to novelty by the unitque combination of a very vigirous, tough, durable and short plant habit, with the ability to grow well as a multiple stem and multiple bloom plant, a very vigorous and extensive root system, stiff stems which do not require staking, retention of the bracts, foliage and inflorescences for a long period of time after reaching maturity, a habit of not requiring light to delay bud set, a well-pinching habit which produces 3 or more breaks, a normal blooming habit at about 4° to 5° lower night temperatures than required for variety "C–1 Red" (Plant Pat. No. 2,923) during the months of October, November and December, but having the ability to be satisfactorily brought into bloom and full maturity in every month of the year through the exercise of proper greenhouse cultural techniques, a distinctive and attractive appearance of the bracts and their absence of any tendency to droop with age, a distinctive and attractive bright Scarlet Red general color tonality of the bracts, absence of drooping and retention of the position of the inflorescences relative to the bracts without rising as occurs in other varieties as their inflorescences approach maturity, and excellent keeping qualities and consequent suitability for home decoration.

No references cited.

ROBERT E. BAGWILL, Primary Examiner